US011529179B2

(12) United States Patent
Deridder et al.

(10) Patent No.: US 11,529,179 B2
(45) Date of Patent: Dec. 20, 2022

(54) BONE MATERIAL DISPENSING SYSTEM WITH LOCKING MEMBER

(71) Applicant: Warsaw Orthopedic, Inc., Warsaw, IN (US)

(72) Inventors: Steven D. Deridder, Bartlett, TN (US); Ralph D. Goosby, Bartlett, TN (US); Erick Vasquez, Memphis, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 395 days.

(21) Appl. No.: 16/879,352

(22) Filed: May 20, 2020

(65) Prior Publication Data
US 2020/0275965 A1 Sep. 3, 2020

Related U.S. Application Data

(62) Division of application No. 16/026,647, filed on Jul. 3, 2018, now Pat. No. 10,687,880.

(51) Int. Cl.
*A61B 17/58* (2006.01)
*A61B 17/60* (2006.01)
(Continued)

(52) U.S. Cl.
CPC ...... *A61B 17/8819* (2013.01); *A61B 17/8808* (2013.01); *A61B 17/8816* (2013.01);
(Continued)

(58) Field of Classification Search
CPC combination set(s) only.
See application file for complete search history.

(56) References Cited

U.S. PATENT DOCUMENTS 3,598,293 A * 8/1971 Lee .................. B05C 17/01
222/391
4,338,925 A 7/1982 Miller
(Continued)

FOREIGN PATENT DOCUMENTS

CN 105147386 A 12/2015
EP 0791404 B1 4/2002
(Continued)

OTHER PUBLICATIONS

European Search Report dated Mar. 3, 2022, issued by the European Patent Office in corresponding European application No. 19830820.7 for Bone Material Dispensing System with Locking Member.

*Primary Examiner* — Sameh R Boles
(74) *Attorney, Agent, or Firm* — Sorell, Lenna & Schmidt, LLP; William D. Schmidt, Esq.

(57) ABSTRACT

A bone material dispensing device is provided. The bone material dispensing device comprises a housing having a proximal end, a distal end, and a longitudinal axis. The proximal end having a first opening and the distal end having a second opening. The first opening and the second opening configured to slidably receive at least a portion of a plunger. A locking member is provided that is pivotably connected to an upper surface of the housing and extends adjacent to the upper surface of the housing. The locking member comprises a locking surface extending adjacent to the distal end of the housing configured to engage a portion of a tubular member, a funnel, or a combination thereof. The locking member is movable in a locking position to lock the portion of the tubular member, the funnel, or the combination thereof with the housing. A bone material dispensing system and a method of implanting bone material with the bone material dispensing system are also provided.

20 Claims, 9 Drawing Sheets

(51) Int. Cl.
*A61F 2/00* (2006.01)
*A61B 17/88* (2006.01)
*A61F 2/46* (2006.01)
*A61B 17/00* (2006.01)

(52) U.S. Cl.
CPC ........ *A61B 17/8822* (2013.01); *A61F 2/4601* (2013.01); *A61B 2017/00407* (2013.01); *A61B 2017/00862* (2013.01)

(56) References Cited

U.S. PATENT DOCUMENTS

| | | |
|---|---|---|
| 5,893,488 A | 4/1999 | Hoag et al. |
| 6,439,439 B1 | 8/2002 | Richard et al. |
| 7,011,238 B1 | 3/2006 | Sung |
| 7,316,689 B2 | 1/2008 | Lieberman |
| 8,845,646 B2 | 9/2014 | Vendrely et al. |
| 2002/0092871 A1 | 7/2002 | Richkard et al. |
| 2004/0193170 A1 | 9/2004 | Kemppainen et al. |
| 2010/0094307 A1 | 4/2010 | Evans et al. |
| 2011/0218513 A1 | 9/2011 | Walker et al. |
| 2013/0168417 A1 | 7/2013 | Gilliam et al. |
| 2014/0324013 A1 | 10/2014 | Shadeck et al. |
| 2015/0112352 A1 | 4/2015 | Kraus et al. |
| 2016/0288161 A1 | 10/2016 | Yi |

FOREIGN PATENT DOCUMENTS

| | | |
|---|---|---|
| EP | 2865341 A1 | 4/2015 |
| EP | 2774583 B1 | 11/2015 |
| JP | 6282977 B2 | 2/2018 |

\* cited by examiner

BONE MATERIAL DISPENSING SYSTEM WITH LOCKING MEMBER

BACKGROUND

Various devices and methods have been used to administer bone material, such as bone graft, to a surgical site. Bone graft is important in orthopedic procedures for the repair of bone defects caused by injury, disease, wounds, or surgery. Toward this end, a number of materials have been used or proposed for use in the repair of bone defects. The biological, physical, and mechanical properties of the materials are among the major factors influencing their suitability and performance in various orthopedic applications.

Conventionally, bone tissue regeneration is achieved by filling a bone defect with a bone material, for example, a bone graft. Over time, the bone graft is incorporated by the host and new bone remodels the bone graft. Bone material can include bone from the patient's own body, synthetic bone material, natural substitute bone material or combinations thereof.

To deliver the bone material to the bone defect, oftentimes the bone material is mixed with liquid or a therapeutic agent, powder, fiber or granular material. Further, transfer of bone material to the dispensing device is often done by crude and messy packing of the bone dispensing device which can cause unwanted waste and spillage of bone material. During transfer and delivery of the bone material, these devices can also increase the risk of contamination of the bone material. Additionally, some dispensing devices can cause damage to surrounding tissue of a surgical site during administration of the bone material. Moreover, bone material can clog certain dispensing devices due to its consistency and/or due to the design of the dispensing device and the amount of bone material cannot be controlled effectively when this occurs.

It would therefore be desirable to provide a bone material dispensing system that includes a reusable bone material dispensing device that allows easier loading of the bone material, which reduces the risk of contamination and spillage of bone material from the dispensing device. It would be useful for a bone material dispensing system to include a bone material dispensing tray that holds the bone material on a surface of the tray while the tray engages the device so that a user can easily load the device and/or a cannula with the bone material. It would also be beneficial to provide a dispensing device that reduces clogging during dispensing of the bone material and is also able to deliver the bone material incrementally in controlled amounts to a bone defect.

SUMMARY

In some embodiments, a bone material dispensing system is provided that reduces the risk of contamination and spillage of bone material from a reusable dispensing device, administers the bone material to a bone defect, and the devices and methods provided reduced clogging during incremental dispensing of the bone material. The bone material dispensing system includes a tray for loading bone material into a bone material dispensing device and/or a cannula.

In some embodiments, a bone material dispensing device is provided. The bone material dispensing device comprises a housing having a proximal end, a distal end, and a longitudinal axis. The proximal end having a first opening and the distal end having a second opening. The first opening and the second opening configured to slidably receive at least a portion of a plunger. A locking member is provided that is pivotably connected to an upper surface of the housing and extends adjacent to the upper surface of the housing. The locking member comprises a locking surface extending adjacent to the distal end of the housing configured to engage a portion of a tubular member, a funnel, or a combination thereof. The locking member is movable in a locking position to lock the portion of the tubular member, the funnel, or the combination thereof with the housing.

In some embodiments, a bone material dispensing system is provided. The bone material dispensing system comprises a bone material dispensing gun comprising a housing having a proximal end, a distal end, and a longitudinal axis. The proximal end has a first opening and the distal end has a second opening. The first opening and the second opening are configured to slidably receive at least a portion of a plunger. The bone material dispensing gun comprises a locking member that is pivotably connected to an upper surface of the housing and extends adjacent to the upper surface of the housing. The locking member comprises a locking surface extending adjacent to the distal end of the housing. The locking member is movable in a locking position to lock the portion of the tubular member, the funnel, or the combination thereof with the housing. The bone material dispensing system comprises a tray that is engageable with the bone material dispensing gun for loading the bone material dispensing gun with bone material.

In some embodiments, a method of implanting a bone material is provided. The method comprises loading a bone material dispensing gun with the bone material from a tray, the bone material dispensing gun comprising a housing having a proximal end, a distal end, and a longitudinal axis, the proximal end having a first opening and the distal end having a second opening, the first opening and the second opening configured to slidably receive at least a portion of a plunger, and a locking member pivotably connected to an upper surface of the housing and extending adjacent to the upper surface from the housing, the locking member comprising a locking surface extending adjacent to the distal end of the housing configured to engage a portion of a tubular member, a funnel, or a combination thereof, the locking member being movable in a locking position, such as a downward position to lock the portion of the tubular member, the funnel, or the combination thereof to the housing, the tubular member being movable in a first position to align the proximal opening of the tubular member or the proximal opening of the tubular member and the funnel with the second opening of the housing to allow the tubular member or the tubular member and the funnel to receive at least the portion of the plunger to dispense the bone material.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying figures.

Figure 1:
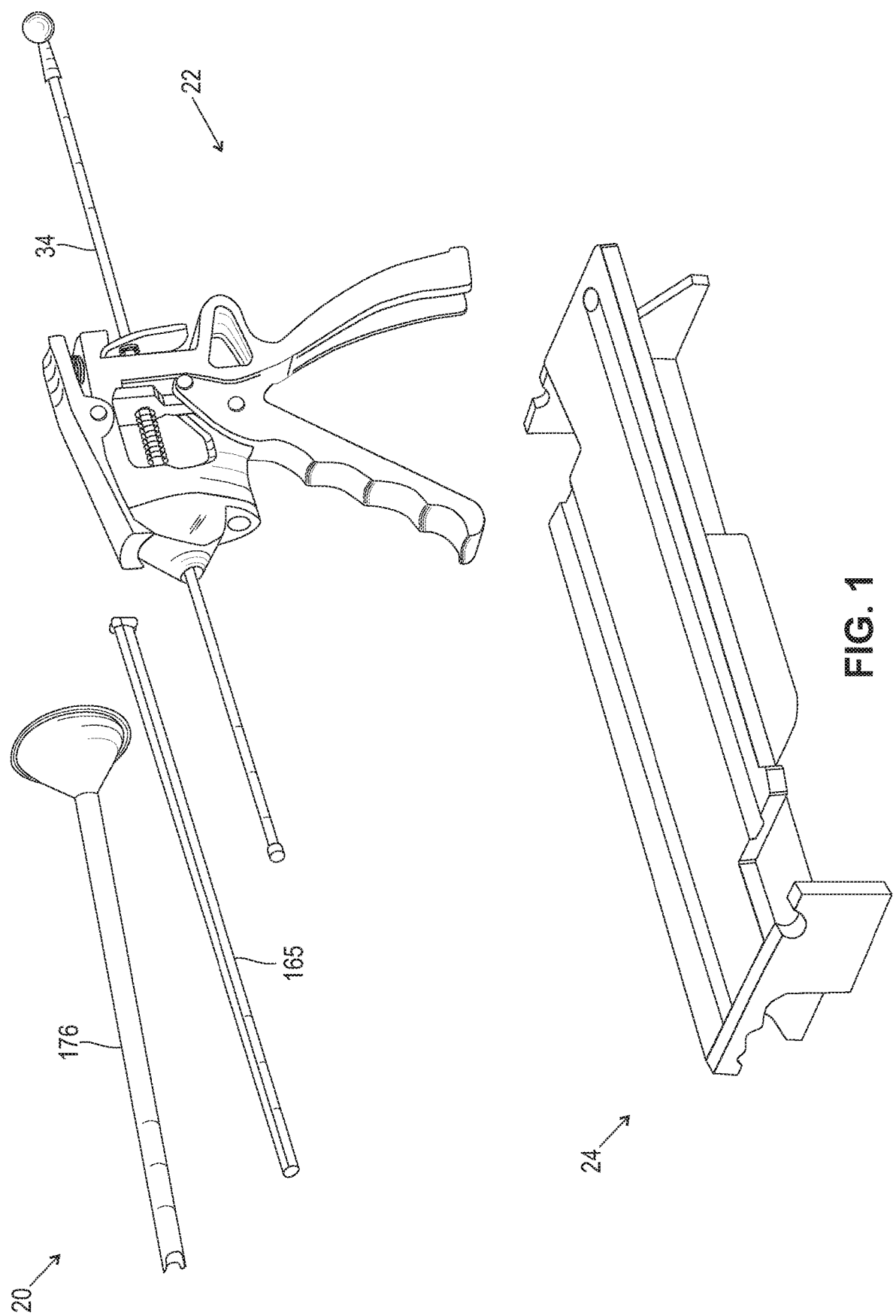
FIG. 1 is a perspective view of a bone material dispensing system according to an aspect of the present application. The bone material dispensing system comprises a bone material dispensing device, a plunger, a funnel, a folding cannula and a tray. The tray is engagable with the bone material dispensing device for loading the bone material dispensing device with bone material.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "xenograft" refers to tissue or organs from an individual of one species transplanted into or grafted onto an organism of another species, genus, or family.

The term "mammal" refers to organisms from the taxonomy class "mammalian," including, but not limited to, humans; other primates, such as chimpanzees, apes, orangutans and monkeys; rats, mice, cats, dogs, cows, horses, etc.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "bone material" includes natural and/or inorganic material such as, for example, inorganic ceramic and/or bone substitute material. The bone material can also include natural bone material such as, for example, bone which is cortical, cancellous or cortico-cancellous of autogenous, allogenic, xenogenic, or transgenic origin. In some embodiments, bone material can include demineralized bone material such as, for example, substantially demineralized bone material, partially demineralized bone material, or fully demineralized bone material.

"Demineralized" as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the application. In some embodiments, demineralized bone has less than 95% of its original mineral content.

In some embodiments, demineralized bone has less than 95% of its original mineral content. In some embodiments, demineralized bone has less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "demineralized" is intended to encompass such expressions as "substantially demineralized," "superficially demineralized," "partially demineralized," "surface demineralized," and "fully demineralized."

"Partially demineralized" is intended to encompass "surface demineralized." "Partially demineralized bone" is intended to refer to preparations with greater than 5% calcium by weight but containing less than 100% of the original starting amount of calcium. In some embodiments, partially demineralized comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

"Superficially demineralized" as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

"Demineralized bone matrix" as used herein, refers to any material generated by removing mineral material from bone tissue. In preferred embodiments, the DBM compositions as used herein include preparations containing less than 5% calcium and preferably less than 1% calcium by weight.

"Biocompatible" as used herein, refers to materials that, upon administration in vivo, do not induce undesirable long-term effects.

"Osteoconductive" as used herein, refers to the ability of a non-osteoinductive substance to serve as a suitable template or substance along which bone may grow.

"Osteogenic", as used herein, refers to the ability of an agent, material, or implant to enhance or accelerate the growth of new bone tissue by one or more mechanisms such as osteogenesis, osteoconduction, and/or osteoinduction.

"Osteoinductive" as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the dispensing systems described herein may obviously be disposed in different orientations when in use.

The term "removably engage" includes engagement of two or more components that can be used or combined into one element via the engagement of the two or more elements with a connecting means, a locking means, or by placing the elements tightly together. The two or more elements may be positioned adjacent to each other and each include a contacting surface.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention is an approximation; the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the disclosure, examples of which are illustrated in the accompanying figures. While the disclosure will be described in conjunction with the illustrated embodiments, it will be understood that they are not intended to limit the disclosure to those embodiments. On the contrary, the disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

Dispensing System

A bone material dispensing system 20, as shown in FIGS. 1-11 is provided that that includes a reusable bone material dispensing device 22 that allows easier loading of bone material, reducing the risk of contamination and spillage of bone material from the bone material dispensing device. The system also provides a bone material dispensing tray 24 that holds the bone material on a surface of the tray while the tray holds the device in place so that a user can easily load the device with the bone material, as described herein.

Figure 11:
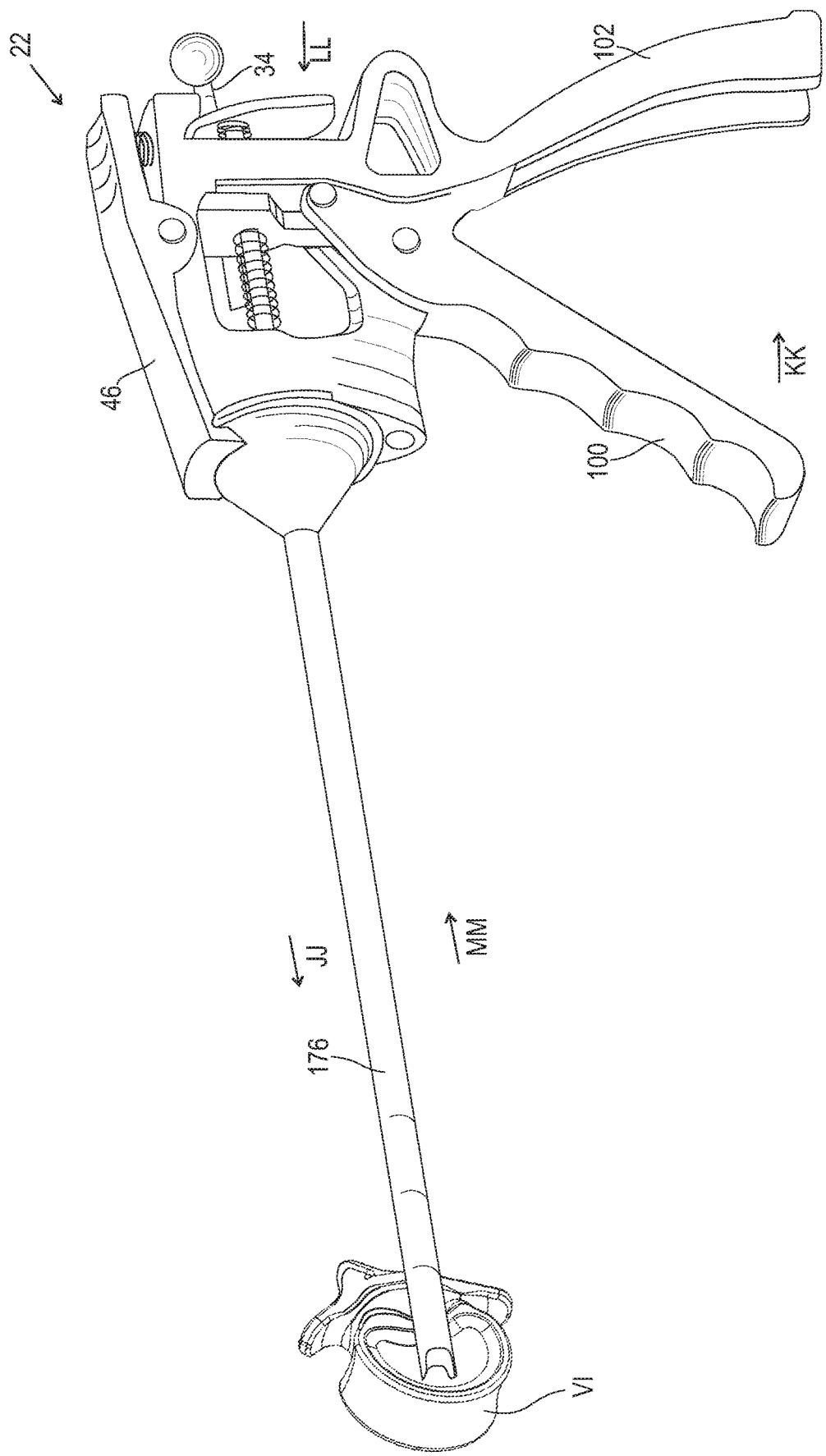
FIG. 11 is a perspective view of the bone material dispensing device of FIG. 2. An end of the funnel is shown adjacent a vertebral disc for administration of the bone material.

The reusable bone material dispensing device administers bone material to a surgical site in incremental amounts. The bone material dispensing device can be a bone material dispensing gun that reduces the risk of contamination and spillage of bone material from the dispensing device, and administers the bone material to a surgical site (e.g., bone defect) while reducing damage to surrounding tissue. The bone material dispensing device reduces clogging and allows incremental dispensing of the bone material. The bone material dispensing device is also configured for left handed and right handed use. A surgical site can include, but is not limited to injury, defects brought about during the course of surgery, infection, malignancy or developmental malformation. Specific bones which can be repaired or replaced with the bone material can include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones. In some embodiments, the bone material dispensing device administers bone material to at least a portion of the spinal cord such as vertebrae or a vertebra V1, as shown in FIG. 11.

Figure 2:
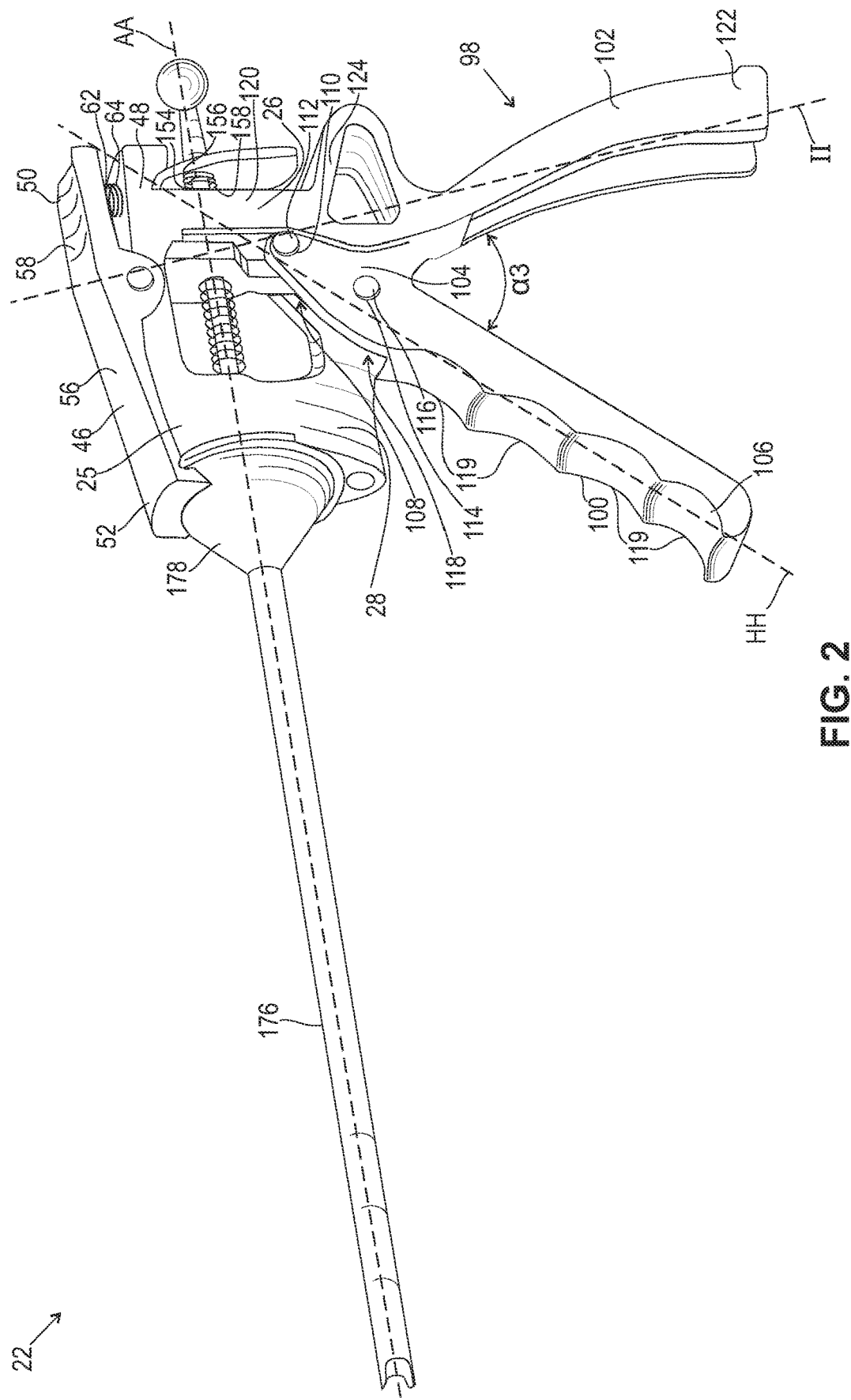
FIG. 2 is a perspective view of the bone material dispensing device according to an aspect of the present application. The bone material dispensing device includes a housing having a proximal end having a first opening, a distal end having a second opening, and a longitudinal axis. The first opening and the second opening are configured to slidably receive at least a portion of a plunger. The bone material dispensing device includes a locking member that is pivotably connected to an upper surface of the housing and extends transversely above the upper surface from at least the proximal end to the distal end of the housing. The locking member comprises a distal end configured to engage a portion of a tubular member, a funnel, or a combination thereof.
Figure 6:
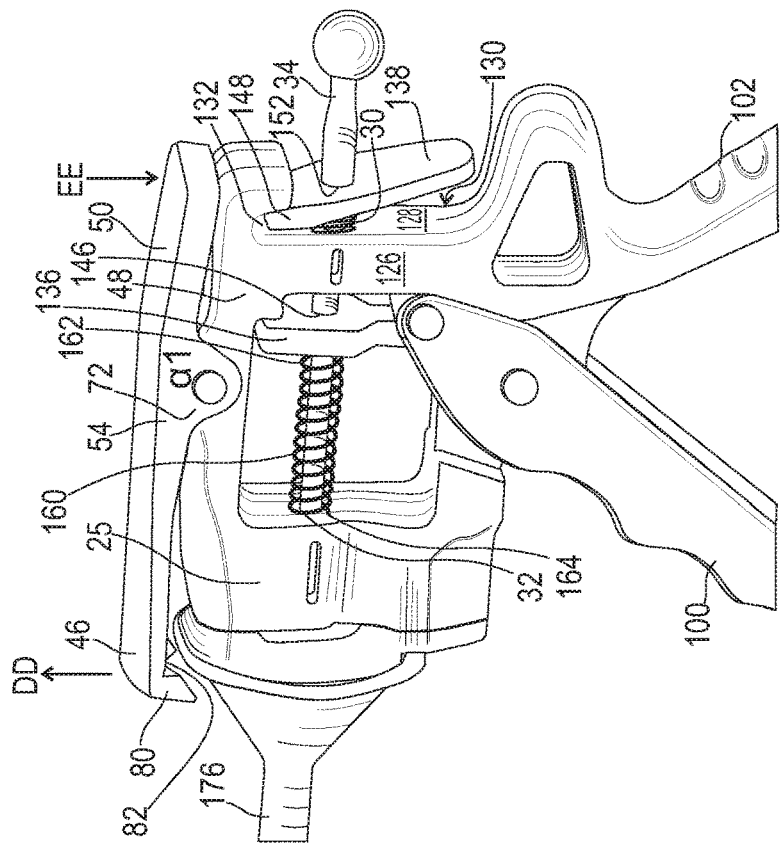
FIG. 6 is an enlarged perspective view of a portion of the bone material dispensing device of FIG. 2 with the housing, locking member shown in the release position, second and third biasing members and plunger shown.

The bone material dispensing device includes a housing 25 having a proximal end 26, a distal end 28, and a longitudinal axis AA disposed therebetween, as shown in FIG. 2. The proximal end of the housing includes a first opening 30 and the distal end includes a second opening 32, as shown in FIG. 6. The first opening and the second opening are configured to slidably receive at least a portion of a plunger 34, as described herein.

Figure 7:
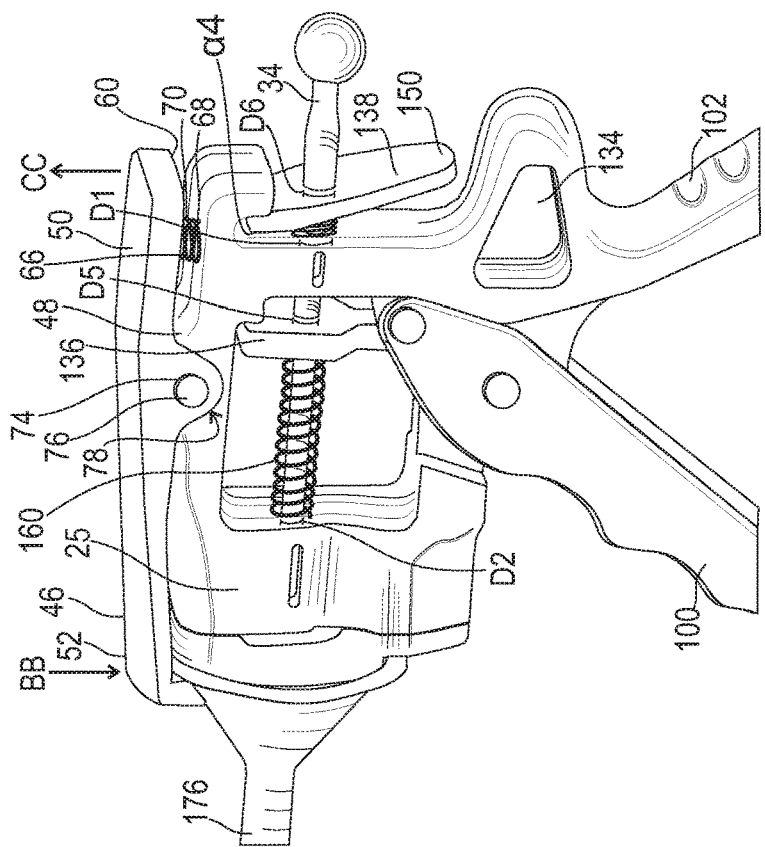
FIG. 7 is an enlarged perspective view of a portion of the bone material dispensing device of FIG. 2 with the housing, locking member shown in the locked position, second and third biasing members and plunger shown.

The first opening has a diameter D1 and the second opening has a diameter D2, as shown in FIG. 7. D1 and D2 are the same diameter. In some embodiments, D1 and D2 can have different diameters. In some embodiments, the diameters D1 and D2 can be from about 2 millimeters (mm) to about 40 mm. The diameters can be from about 2, 4, 6, 8, 10, 12, 14, 16, 18, 20, 22, 24, 26, 28, 30, 32, 34, 36, 38 to about 40 mm. The first and second openings can be shaped and can be round, oval, rectangular or square.

The plunger, as described herein, has a proximal end 36, a distal end 38 and a body 40 disposed therebetween. The plunger is configured to assist in the dispensing/administration of the bone material to a surgical site, as described herein. This allows for controlled and incremental administration of the bone material to the bone defect. The proximal end of the plunger includes a stopper 42 that is configured to prevent the plunger from passing entirely through the first and second openings of the housing when the plunger is translated in the direction of the distal end of the housing. In some embodiments, the stopper can be ball shaped and have a diameter that is greater than diameters D1 and D2. In some embodiments, the distal end of the plunger can include a tip 44 having various geometries and sizes that are tailored for various sized cannulas, as described herein, and/or for varying viscosities of bone material, as described herein. In some embodiments, the tip of the plunger can be square, rectangular, round, plug, or disc shaped.

Figure 5:
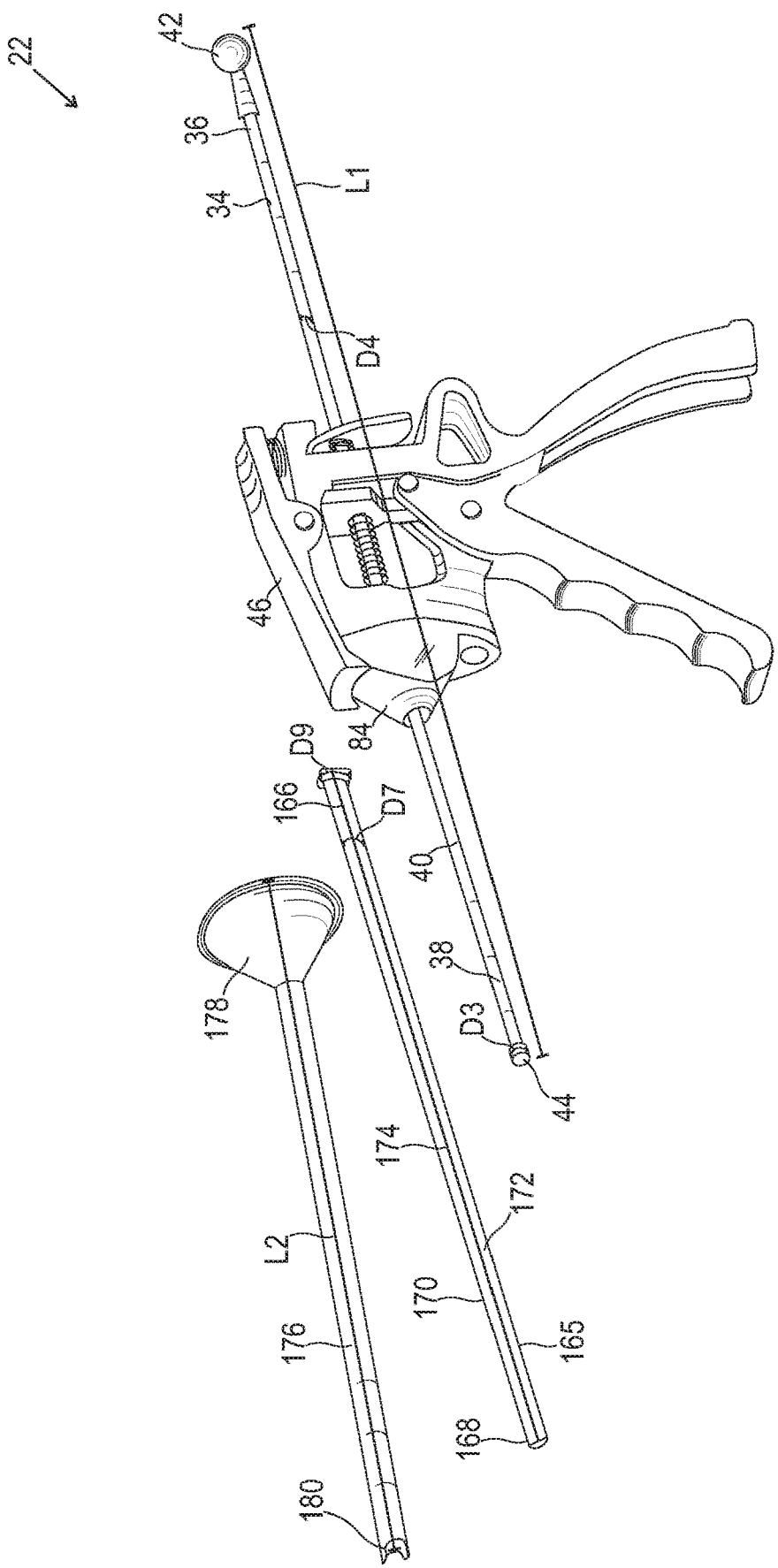
FIG. 5 is a perspective view of the bone material dispensing device of FIG. 2. The funnel and folding cannula are shown separated from the device.

The tip can have a diameter D3 and the body can have a diameter D4, as shown in FIG. 5. In some embodiments, diameter D3 is larger than diameter D4. In some embodiments, diameters D3 and D4 are the same size. Diameter D4 of the body of the plunger is smaller than diameters D1 and D2, and diameter D3 can be larger, the same or less than diameters D1 and D2. In some embodiments, the diameter D4 of the body of the plunger is slightly smaller than diameters D1 and D2 but allows at least a portion of the plunger to slide within the openings. In some embodiments, diameters D3 and D4 can be from about 2 millimeters (mm) to about 36 mm. The diameters D3 and D4 can be from about 2, 4, 6, 8, 10, 12, 14, 16, 18, 20, 22, 24, 26, 28, 30, 32, 34 to about 36 mm. The plunger can also have a certain length L1 of from about 1 to about 20 inches, as shown in FIG. 5. In some embodiments, the length L1 of the plunger can be from about 1, 2, 3, 4, 5, 6, 7, 8, 9, 10, 11, 12, 13, 14, 15, 16, 17, 18, 19 to about 20 inches. The plunger length can be smaller, larger or the same size as the cannula, as described herein. In some embodiments, the plunger can be flexible or rigid.

The bone material dispensing device includes a locking member 46. The locking member is configured to lock a portion of a tubular member, and/or a funnel, as described herein, to the housing of the bone material dispensing device. The locking member is pivotably connected to an upper surface 48 of the housing and extends adjacent to the upper surface of the housing, as shown in FIGS. 2, 6 and 7. The locking member includes a proximal end 50 configured to engage with a biasing member, as described herein, and a distal end 52 configured to engage with a portion of the tubular member, and/or the funnel, as described herein, and an intermediate portion 54 disposed therebetween configured to pivotably engage with a portion of the upper surface of the housing.

The locking member is movable in a locking position, such as a downward position, to lock the portion of the tubular member, the funnel, or the combination thereof with the housing, and the locking member is movable in an unlocking position, such as an upward position, to unlock the portion of the tubular member, the funnel, or the combination thereof from the housing, as described herein.

The proximal end of the locking member includes an outer surface 56 that includes in some embodiments, a gripping surface 58 that provides a grip for a user when the user pushes downward on the proximal end of the locking member during use. An interior surface 60 of the locking member defines a stanchion 62 disposed at the proximal end that is configured for engagement with a first end 66 of a first resilient member, such as a first spring 64, as shown in FIGS. 2 and 7. A portion of the upper surface of the proximal end of the housing includes a recess 68 configured for engagement with a second end 70 of the first spring. The stanchion and the recess are configured for engagement with the first spring.

The intermediate portion of the locking member includes a pivot point 72 engaged with the upper surface of the housing. The pivot point includes an opening 74, a pin 76 and an opening 78 formed from a portion of the upper surface of the housing, as shown in FIGS. 6 and 7. The pin is configured for disposal within openings 74 and 78. In some embodiments, the pivot point pivots at an angle α1 of about 1 degree to about 30 degrees. In some embodiments, the pivot point pivots at an angle α1 of about 1, 2, 3, 4, 5, 6, 7, 8, 9, 10, 11, 12, 13, 14, 15, 16, 17, 18, 19, 20, 21, 22, 23, 24, 25, 26, 27, 28, 29 to about 30 degrees.

The distal end of the locking member includes a locking surface, such as a flange 80 that extends adjacent to the distal end of the housing. The flange locks a portion of the tubular member, funnel or the combination thereof with the housing of the bone material dispensing device. As shown in FIG. 6, the flange can include an inner surface that is grooved 82 to facilitate engagement with a portion of the tubular member and/or the funnel.

The flange at the distal end of the locking member is moved in a downward position, as shown by arrow BB in FIG. 7 to lock the portion of the tubular member, the funnel, or the combination thereof with the housing. When the flange is in the downward position, the proximal end is positioned in an upward direction, as shown by arrow CC. In this configuration, the first spring is partially compressed with the stored energy applying constant force against both stanchion 62 and recess 68. The flange unlocks the tubular member, funnel, or the combination thereof when the flange is moved in an upward position, as shown by arrow DD in FIG. 6, when the user pushes the proximal end of the locking member in a downward direction, as shown by arrow EE. In this configuration, the first spring is further compressed and energy is stored for use when the locking member is moved again in the downward position, as described above.

Figure 4:
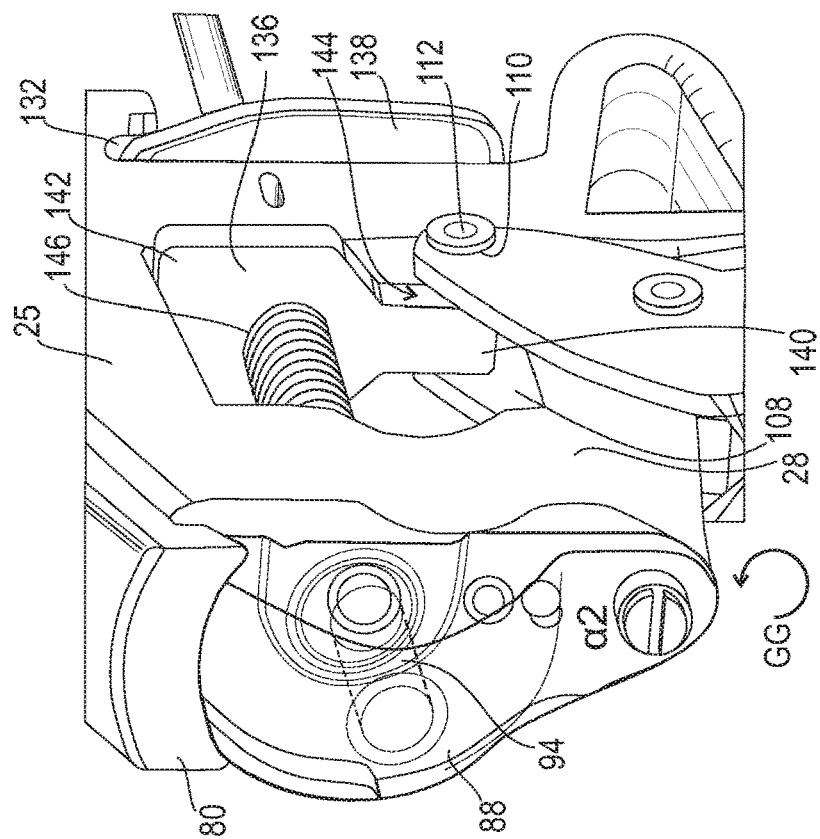
FIG. 4 is an end view partially in phantom of the bone material dispensing device of FIG. 1 with the tubular member shown in phantom.
Figure 3:
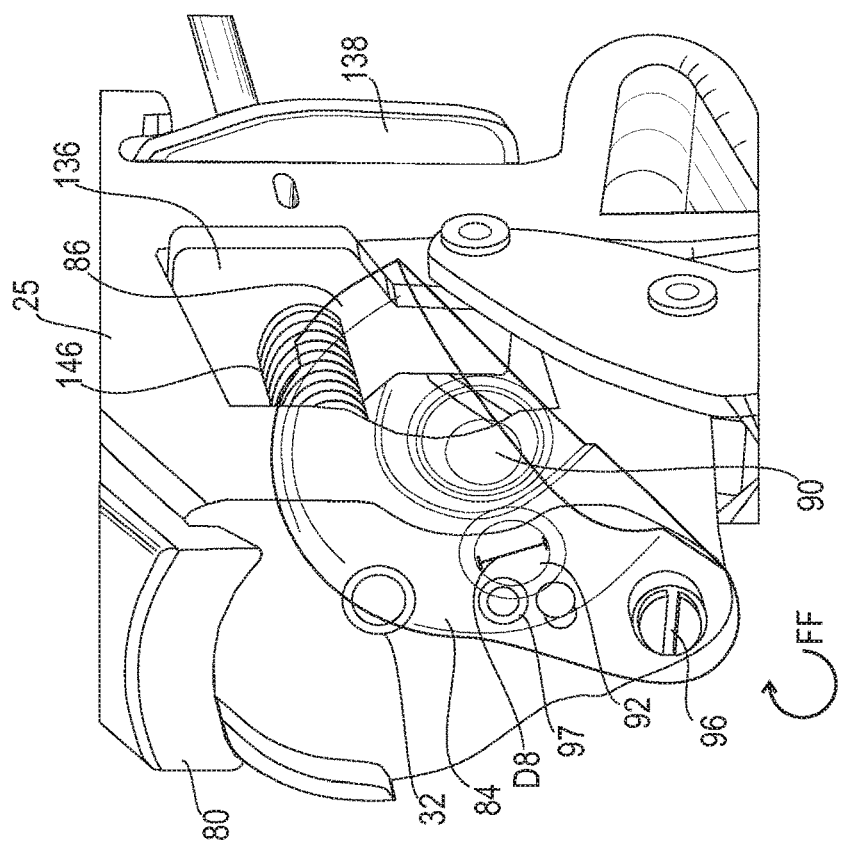
FIG. 3 is an end view partially in phantom of the bone material dispensing device of FIG. 1 with the tubular member shown in phantom.

The bone material dispensing device includes a tubular member 84 that is pivotably connected to the housing and is configured for radial movement relative to longitudinal axis AA of the housing. As shown in FIGS. 2-4, the tubular member includes a proximal end 86, a distal end 88 and the longitudinal axis AA is disposed therebetween when the tubular member is in a first position, as described herein. The tubular member can be conical and the distal end can be tapered.

The proximal end of the tubular member includes a proximal opening 90 and the distal end of the tubular member includes a distal opening 92. A channel 94 is disposed therebetween. The proximal opening, the distal opening and the channel of the tubular member are configured to receive at least a portion of the plunger such that when bone material is disposed within the channel, the plunger can be advanced into the channel to dispense or administer the bone material, as described herein. For example, the tubular member is movable in a first position to align the proximal opening of the tubular member with the second opening of the housing to allow the tubular member to receive at least the portion of the plunger (as shown in FIG. 4) to dispense the bone material. The tubular member is also movable in a second position to misalign the proximal opening of the tubular member with the second opening of the housing to prevent the tubular member from receiving at least the portion of the plunger (as shown in FIG. 3).

As described above, the tubular member is pivotably connected to the housing via a pivot point, such as a hinge 96. The hinge is transverse relative to longitudinal axis AA. The hinge facilitates rotation of the tubular member relative to the housing in the directions shown by arrows FF and GG, shown in FIGS. 3 and 4. The hinge can alternatively be or can include a pivot pin, or a rod. The tubular member pivots towards and away from the housing at an angle α2 of from about 2 to about 320 degrees, as shown in FIG. 4. In some embodiments, α2 is from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318 to about 320 degrees. The tubular member can be pivoted so that there is enough space provided for the tubular member to be loaded with bone material.

The tubular member locks with a portion of the distal end of the housing via a detent 97 and/or the flange of the locking member. The detent is located on a portion of the distal end of the housing. The detent locks the tubular member in the first position, as described above. The detent can be a catch, a lever, a spring, or a hinged catch that engages a notch of a ratchet, a protrusion, wall, or a combination thereof. The locking will allow the openings to align (as shown in FIG. 4) and the plunger to be slid through the openings. In some embodiments, when the tubular member is swiveled open, the holes are misaligned and the plunger cannot be slid through the tubular member, as shown in FIG. 4.

In some embodiments the tubular member can be entirely detachable and can snap connect to the housing. In some embodiments, the tubular member can be entirely detachable and connect with a screw-on thread form to the housing. In some embodiments, the tubular member can be pivotably connected to the housing in a similar manner to a breach loaded shot-gun. It should be noted that one of ordinary skill in the art can modify the tubular member and its connection to the housing to adjust the design of the bone material dispensing device.

The housing includes a trigger assembly 98, as shown in FIG. 2, that is configured to allow incremental slidable movement of the plunger to dispense the bone material, as described herein. The trigger assembly includes a driving handle 100 and a stationary handle 102. The driving handle includes a proximal end 104, a distal end 106 and a longitudinal axis HH disposed therebetween. The proximal end of the driving handle is configured for pivotable engagement with an intermediate portion of the stationary handle and a proximal end of a driving pawl, as described below. The proximal end of the driving handle includes a cavity 108, as shown in FIGS. 2 and 4. The cavity is configured for movable engagement with a portion of the driving pawl, as described herein.

The proximal end of the driving handle and transverse to the cavity includes a recess 110. The recess is configured for engagement with a pin 112 such that the proximal end of the driving handle pivotably engages with a portion of the driving pawl, as described herein. The proximal end of the driving handle and distal to recess 110, includes a recess 114, as shown in FIG. 2. The recess is configured for engagement with a pin 116 such that the proximal end of the driving handle is movably engaged with a portion of the housing. The housing includes a recess 118 configured to engage with pin 116.

A surface of the driving handle includes gripping surfaces 119. The gripping surfaces are configured for engagement with a user's hand such that the driving handle can be controlled effectively by the user. The gripping surfaces can be raised, curved or straight. The gripping surface can also be roughened to increase the control that the user has over the driving handle.

The user moves the driving handle in the direction of the stationary handle. The driving handle engages the active pawl, which slides the plunger longitudinally and incrementally in the direction of the distal end. This allows for bone material to be incrementally dispensed from the bone material dispensing device.

Figure 9:
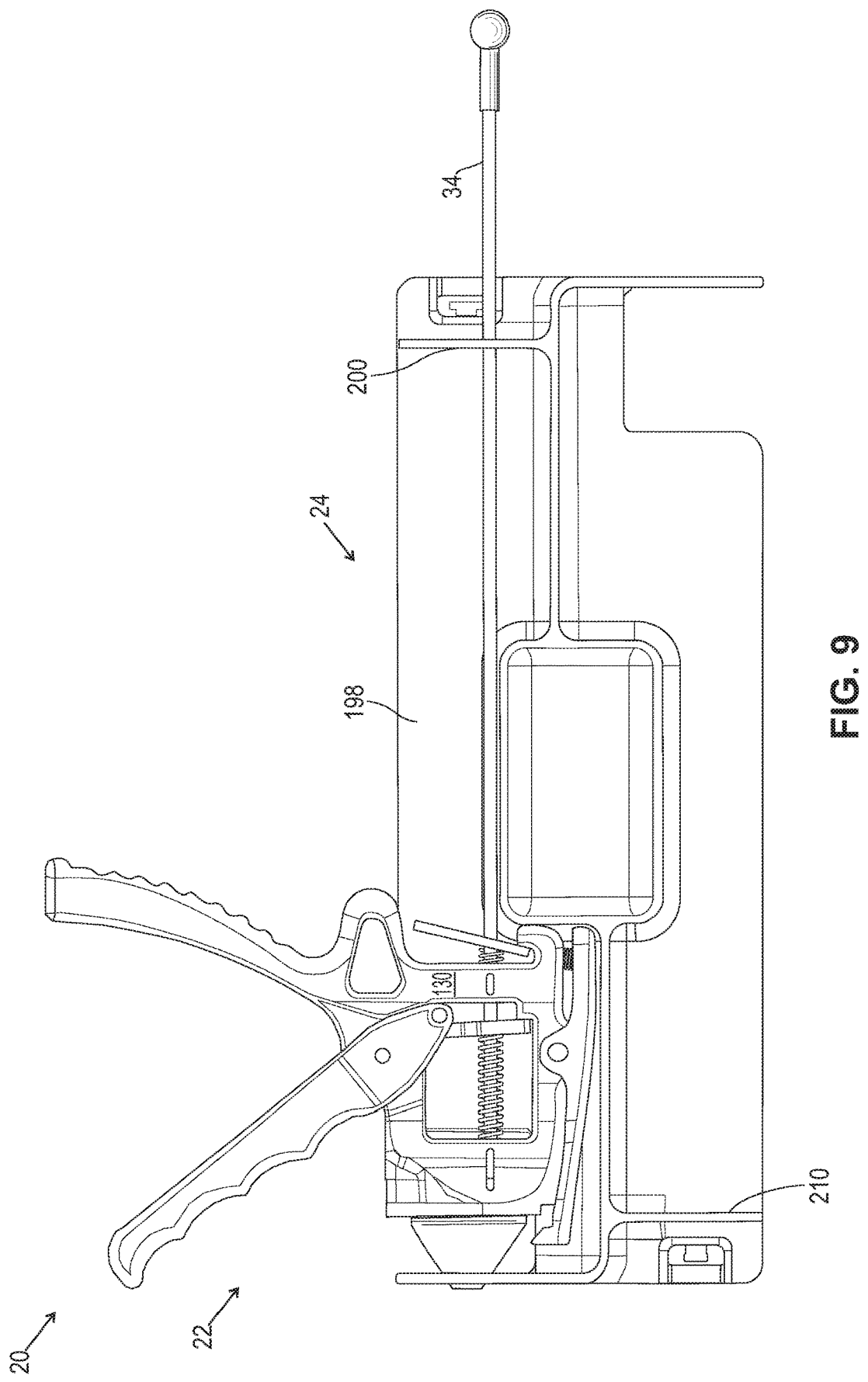
FIG. 9 is a bottom view of the bone material dispensing system of FIG. 1 where the bone material dispensing device is engaged with the tray for loading the bone material dispensing device with bone material. The funnel and the folding cannula is not shown in this FIG.

The stationary handle includes a proximal end 120, a distal end 122, an intermediate portion 124 and a longitudinal axis II disposed between the proximal end and the distal end. The proximal end of the stationary handle includes a first side 126, a second side 128 and a third side 130, as shown in FIGS. 6 and 9. The first, second and third sides are part of the housing. The proximal end of the stationary handle can be monolithic with the housing and the first, second and third sides can be monolithic or fixed to the stationary handle. The intermediate portion of the stationary handle can be monolithic with the housing, and the intermediate portion can be inserted into the cavity of the driving handle. The second side includes a slot 132 that is configured for engagement with a portion of a passive pawl, as described herein and shown in FIG. 4. In some embodiments, the stationary handle and the housing are monolithic with one another. In some embodiments, the stationary handle and the housing are not monolithic.

The intermediate portion of the stationary handle is configured for engagement with the proximal end of the driving handle. The driving handle pivots toward and away from the stationary handle at an angle α3 from about 1 to about 60 degrees, shown in FIG. 2. In some embodiments, α3 is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 degrees.

The stationary handle defines one or more cutouts 134, as shown in FIG. 7. The cutouts can be oval, round, square, triangular, rectangular or any other regular or irregular shape. There can be one or more cutouts formed from the surface of the stationary handle, such as 1, 2, 3, 4, 5, 6 or more cutouts.

The trigger assembly of the housing further includes a driving pawl 136 and a passive pawl 138, as shown in FIGS. 6 and 7. The driving pawl is configured to work in conjunction with a resilient member to assist the stationary handle and the driving handle in incremental slidable movement of the plunger such that the plunger dispenses the bone material. In the embodiment shown in FIG. 6, the resilient member shown as a spring is concentric with the plunger. On movement of the driving handle to the stationary handle, pawl 136 engages plunger 34 and pushes the plunger longitudinally in increments while simultaneously compressing the spring. The driving pawl is disposed at one end of the resilient member and the other end of the resilient member biases against the housing and plunger. Once the driving handle is released, the stored energy in the spring returns the driving handle and pawl longitudinally to their original positions.

The driving pawl includes a first end 140 and a second end 142, as shown in FIG. 4. The first end of the driving pawl is configured for movable engagement within the cavity of the driving handle. Recess 110 and a recess 144 disposed within the first end of the driving pawl, engage with pin 112 such that the proximal end of the driving handle pivotable engages with the first end of the driving pawl. The driving pawl includes a third opening 146 that is in alignment and in between the first opening and the second opening of the housing, as shown in FIGS. 3 and 4. The third opening is configured to slidably receive at least a portion of the plunger, as described herein. The third opening can be centrally located on the driving pawl.

The third opening has a diameter D5, as shown in FIG. 7. D5 can be the same diameter as D1 and D2, and D5 has a greater diameter than plunger diameter D4. In some embodiments, D5 can have a different diameter than D1 and D2. In some embodiments, diameter D5 can be from about 6 millimeters (mm) to about 40 mm. Diameter D5 can be from about 6, 8, 10, 12, 14, 16, 18, 20, 22, 24, 26, 28, 30, 32, 34, 36, 38 to about 40 mm. The third opening can be shaped and can be round, oval, rectangular or square.

The passive pawl includes a first end 148, and a second end 150, as shown in FIGS. 6 and 7. The first end is configured for engagement with slot 132. The passive pawl is configured to work in conjunction with a resilient member to control when the plunger is advanced during dispensing of the bone material and retracted after dispensing or reloading of the bone material. The passive pawl allows the plunger to be adjusted so that the plunger can be located adjacent to the bone material and if more bone material is added to the cannula or the tubular member, the plunger can be adjusted to be placed adjacent to the additional bone material. In this way, the bone material dispensing device can easily accommodate various quantities of bone material.

The passive pawl can pivot at an angle $\alpha 4$ of from about 2 to about 45 degrees, as shown in FIG. 7. In some embodiments, $\alpha 4$ is from about 1, 2, 4, 6, 8, 10, 12, 14, 16, 18, 20, 22, 24, 26, 28, 30, 32, 34, 36, 38, 40, 42, 44, 45 or from about 46 degrees.

The passive pawl includes a fourth opening 152 that is above and in alignment with the first opening and the second opening of the housing, and the third opening of the driving pawl, as shown in FIGS. 6 and 7. The fourth opening is configured to slidably receive at least a portion of the plunger, as described herein. The fourth opening can be centrally located on the passive pawl.

The fourth opening has a diameter D6, as shown in FIG. 7. D6 can be the same diameter as D1, D2 and D5, and has a greater diameter than plunger diameter D4. In some embodiments, D6 can have a different diameter than D1, D2 and D5. In some embodiments, diameter D6 can be from about 6 millimeters (mm) to about 40 mm. Diameter D6 can be from about 6, 8, 10, 12, 14, 16, 18, 20, 22, 24, 26, 28, 30, 32, 34, 36, 38 to about 40 mm. The fourth opening can be shaped and can be round, oval, rectangular or square.

The trigger assembly includes a second resilient member, such as a second spring 154, as shown in FIG. 2 that is configured for engagement with the passive pawl and a portion of the plunger, as described herein. The second spring is disposed on a portion of the plunger and between the second side 128 of the stationary handle and the passive pawl, as shown in FIGS. 2 and 6. The second spring comprises a proximal end 156 configured for engagement with an underside of the passive pawl and a distal end 158 which engages with the second side 128 of the stationary handle and the first opening 30 of the housing. The second spring is concentric with the fourth opening of the passive pawl, and is concentric to the plunger. On moving the passive pawl toward the stationary handle, the second spring can be compressed and store energy, which will allow the plunger to be withdrawn or adjusted to allow bone material to be added to the cannula.

The trigger assembly includes a third resilient member, such as third spring 160 that is configured for engagement with the driving pawl, as described herein. The third spring is disposed concentric to the plunger and is disposed between a portion of the distal end of the housing and the driving pawl, as shown in FIGS. 6 and 7. The third spring comprises a proximal end 162 that engages with a distal surface of the driving pawl, and a distal end 164 that engages with the second opening 32 of the housing. At least a portion of the plunger is configured to be slidably received by the third spring, as described herein.

In some embodiments, the tubular member is configured to engage with a cannula, such as, for example, a folding cannula 165, as shown in FIGS. 1 and 5. The folding cannula is similar to the foldable container found and fully described in U.S. application Ser. No. 15/581,817, of which is owned by Applicant and incorporated fully herein by reference. The folding cannula is configured to be loaded with the bone material and engages the tubular member, the funnel and/or the plunger for dispensing the bone material into a surgical site. The folding cannula comprises a proximal end 166 and a distal end 168. The folding cannula is segmented into an upper compartment 170 and a lower compartment 172, and the folding cannula is movable in a folded configuration and an unfolded configuration about a fold line 174.

The folding cannula has a diameter D7 that is smaller than a diameter D8 of distal opening 92 of the tubular member so as to allow at least a portion of the folding cannula to be held within the tubular member, as shown in FIGS. 3 and 5. In some embodiments, diameter D7 can be from about 2 millimeters (mm) to about 40 mm. The diameter D7 can be from about 2, 4, 6, 8, 10, 12, 14, 16, 18, 20, 22, 24, 26, 28, 30, 32, 34, 36, 38 to about 40 mm. The folding cannula can have differing diameters throughout the folding cannula and does not have to have a uniform diameter. The diameter D8 has a larger diameter than the plunger diameter D4. The diameter D8 can be from about 2, 4, 6, 8, 10, 12, 14, 16, 18, 20, 22, 24, 26, 28, 30, 32, 34, 36, 38 to about 40 mm.

In some embodiments, the proximal end of the folding cannula can have various geometries and sizes. In some embodiments, the proximal end of the folding cannula can be square, rectangular, round, plug, or disc shaped. The proximal end geometry of the folding cannula can have a diameter D9 that is larger than diameters D7 and D8 such that the proximal end geometry cannot pass the distal opening 92 of the tubular member. In some embodiments, the diameter D9 can be from about 6, 8, 10, 12, 14, 16, 18, 20, 22, 24, 26, 28, 30, 32, 34, 36, 38 to about 40 mm.

In some embodiments, the folding cannula engages with a funnel 176 that is configured to removably engage and partially enclose the tubular member, as shown in FIGS. 2, 6, 7 and 11. A proximal portion 178 of the funnel matingly engages conically with the distal end of the tubular member. The proximal end engages with the locking member to lock the funnel to the housing, as described above. As shown in FIG. 5, the funnel portion includes a distal end 180. In some embodiments, the distal end of the funnel has a tip geometry, for example, a tip geometry that is indented to assist in the administration of the bone material to the surgical site. The distal end of the funnel can be variously dimensioned.

The funnel has a length L2, such as about 1 to about 20 inches. In some embodiments, the length of the funnel can be from about 1, 2, 3, 4, 5, 6, 7, 8, 9, 10, 11, 12, 13, 14, 15, 16, 17, 18, 19 to about 20 inches. In some embodiments, the funnel is flexible or rigid, or only one of the funnel or the plunger is flexible.

The bone material dispensing system includes tray 24, as described above and shown in FIGS. 1 and 8-10. The tray is configured for loading bone material into the bone material dispensing device and/or the folding cannula. The tray also is configured to dock the bone material dispensing device and/or the folding cannula for loading of the bone material. The tray includes a proximal end 182 and a distal end 184. A first side 186 is disposed at the proximal end of the tray, and a second side 188 is disposed at the distal end of the tray. The tray includes a third side 190 disposed transverse relative to the first side and the second side, and a fourth side 192 disposed transverse relative to the first side and the second side, and parallel to the third side.

Figure 8:
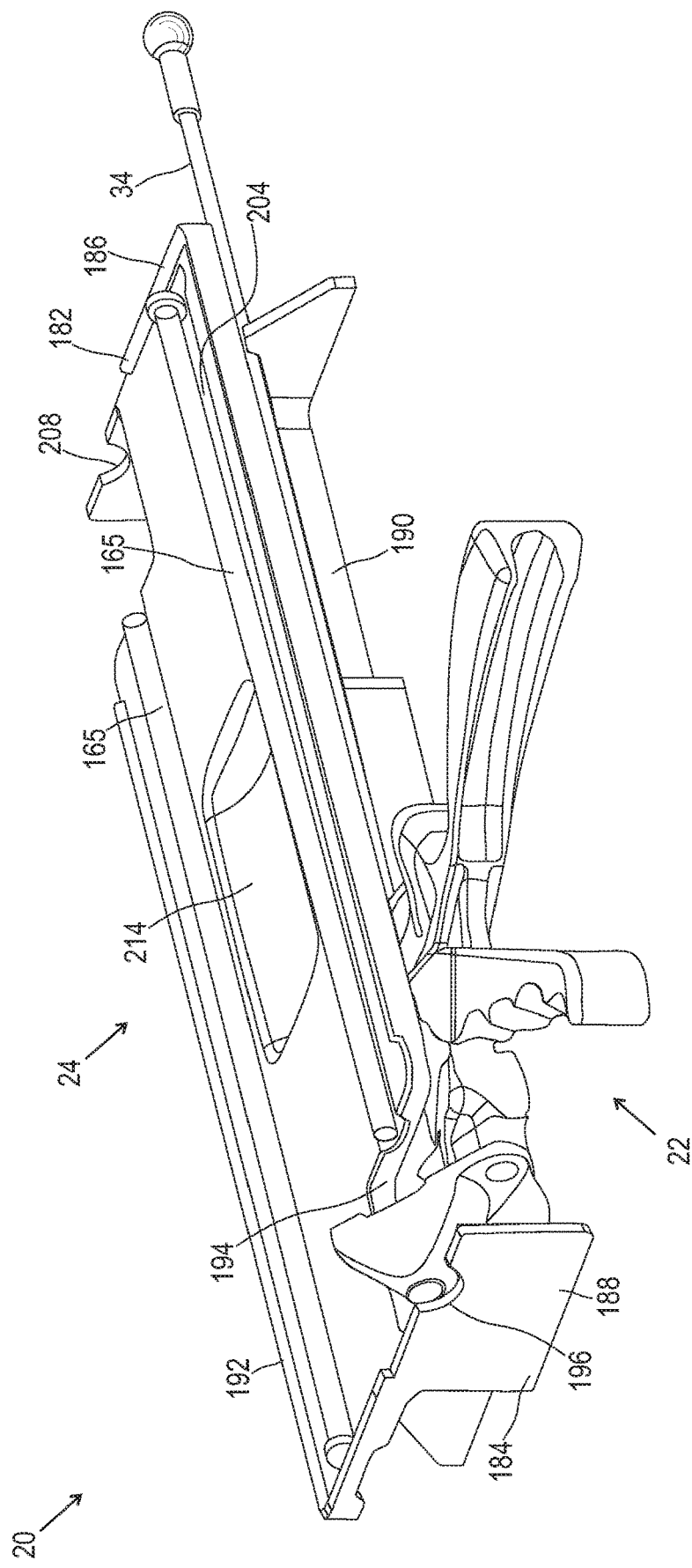
FIG. 8 is a perspective view of the bone material dispensing system of FIG. 1 where the bone material dispensing device is engaged with the tray for loading the bone material dispensing device with bone material. The funnel is not shown in this FIG.

The third side of the tray is configured to engage with the bone material dispensing device, as described herein. A slot, such as first slot 194 is defined from the third side and a portion of the second side, as shown in FIG. 8. The first slot is configured to receive the tubular member, and a first indent 196 is defined from a portion of the second side to engage with a portion of the distal end of the tubular member such that the tubular member rests or docks within the first slot. A lower surface 198 of the tray, as shown in FIG. 9, defines a first ledge 200 that is configured for engagement with a portion of the plunger. When the tubular member of the bone material dispensing device is docked in the first slot, a portion of the plunger is positioned on the first ledge.

Figure 10:
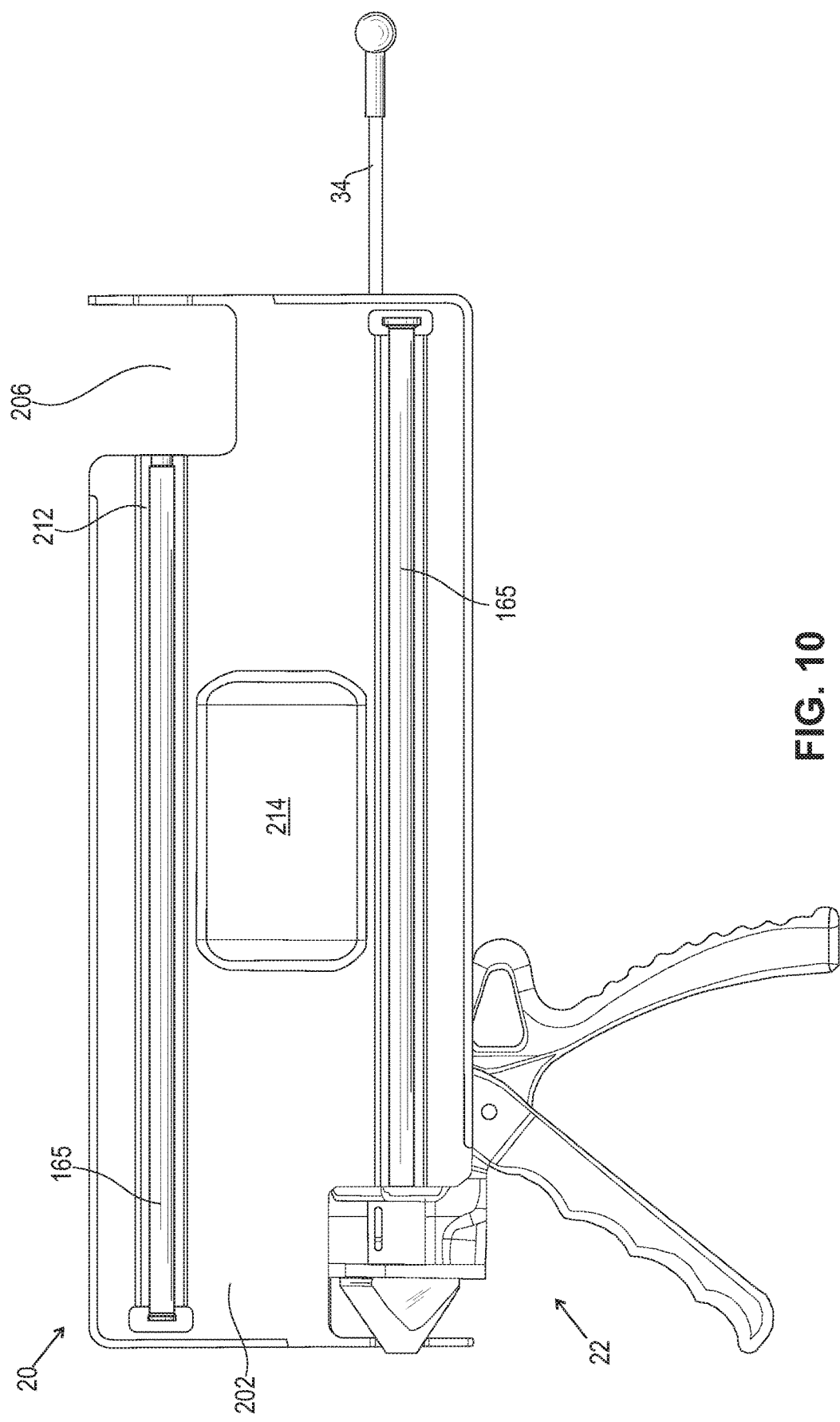
FIG. 10 is a top view of the bone material dispensing system of FIG. 1 where the bone material dispensing device is engaged with the tray for loading the bone material dispensing device with bone material. The funnel is not shown in this FIG.

The tray includes an upper surface 202, as shown in FIG. 10 that defines a first groove or first channel 204. The first groove or first channel is configured to receive a folding cannula. The folding cannula can be placed into the first groove or first channel and loaded with the bone material. Once the folding cannula is loaded, it can then be inserted into the tubular member of the bone dispensing device or it can be inserted into both the tubular member and the funnel.

A second slot 206 is defined from the fourth side and a portion of the first side, as shown in FIG. 10. The second slot can also be configured to receive the tubular member and/or a container for storing bone material, as described herein. A second indent 208 is defined from a portion of the first side to engage with a portion of the distal end of the tubular member such that the tubular member rests or docks within the second slot. The lower surface 198 of the tray, as shown in FIG. 9, defines a second ledge 210 that is configured for engagement with a portion of the plunger. When the tubular member of the bone material dispensing device is docked in the second slot, a portion of the plunger is positioned on the second ledge. The upper surface 202 of the tray, as shown in FIG. 10, defines a second groove or second channel 212. The second groove or second channel is configured to receive a folding cannula. It is to be noted that the system can include one or more folding cannulas.

The upper surface of the tray includes a mixing surface 214. In some embodiments, the mixing surface is defined by the upper surface and is positioned in the center of the upper surface of the tray, as shown in FIGS. 8 and 10. The mixing surface is configured for a user to mix the bone material and other components together (e.g., therapeutic agent, diluent, blood, cells, etc.). The mixing surface can have a bowl configuration to allow mixing solids and liquid components of the bone material. It will be understood by those of ordinary skill in the art that the bone material can be in the form of a powder, granules, paste, putty, liquid, and/or a gel. To mix components and/or dispense the bone material, the bone material dispensing system, in some embodiments, can include a spatula.

In operation, to load the bone material dispensing device with bone material, the bone material dispensing device is docked or attached to the tray, as described above. The tubular member is rotated in the direction of arrow FF, as shown in FIG. 3. The tubular member is then loaded with the bone material, or the folding cannula is loaded with the bone material and inserted into the proximal end of the tubular member so that at least a portion of the folding cannula is held within the tubular member and at least a portion of the folding cannula is fed through the distal opening of the tubular member. The tubular member is then moved about hinge 96 in a first position, as shown by arrow GG in FIG. 4 and the funnel engages with the tubular member and/or the combination tubular member and the folding cannula. The funnel is then locked onto the housing via the locking member, as shown in FIG. 7 when the user places the locking member in the locking position or downward position, as shown by arrow BB. In some embodiments, instead of the tubular member being loaded with the bone material, the funnel can be loaded with the bone material and then locked onto the housing.

The distal end of the funnel is then inserted into a surgical site, such as, for example, vertebra V1, as shown in FIG. 11. The distal end of the funnel can be inserted into the surgical site before or after the funnel is locked onto the housing. For example, the funnel can be placed at the surgical site first and then locked with the housing. In the first position, the proximal opening of the tubular member is aligned with the second opening of the housing to allow the tubular member to receive at least the portion of the plunger to dispense the bone material. The plunger is then translated in the direction of arrow JJ shown in FIG. 11, into the fourth opening of the passive pawl, the first opening of the housing, the third opening of the driving pawl and the second opening of the housing via the trigger assembly.

The driving handle of the trigger assembly moves the driving pawl when the driving handle is moved toward the stationary handle in the direction shown by arrow KK in FIG. 11. Movement of the driving handle toward the stationary handle causes the driving pawl to compress the third spring in the direction shown by arrow JJ. Incremental slidable movement of the plunger is determined via incremental movement of the driving handle toward the stationary handle. Since diameter D5 of the third opening of the driving pawl is slightly larger than diameter D4 of the plunger, and the driving pawl is driven off axis via the driving handle, as the driving handle presses downward, the driving pawl tilts and diameter D5 becomes the same size as diameter D4, pinching the plunger. Any further advancement of the driving handle results in the driving pawl pinching the plunger harder and advancing the plunger. As soon as the pressure on the driving handle is released, the third spring pushes up on the driving pawl again increasing the size of D5, allowing the driving pawl to slide back up the plunger, returning it to the starting position to push again.

Movement of the driving handle toward the stationary handle also causes the second spring to be compressed against the second side of the housing by the passive pawl. The driving handle is released and the driving handle moves in the direction shown by arrow JJ of FIG. 11. The second end of the passive pawl is then pushed in a downward direction, as shown by arrow LL in FIG. 11 to again compress the second spring so that the second spring contains transient energy such that the user can retract the plunger in a proximal direction, as shown by arrow MM of FIG. 11. The advancement and retraction of the plunger can be controlled by the passive pawl and the second spring. For example, the passive pawl pinches the plunger, preventing the plunger from retracting while the driving pawl is returned to its starting position. Further, the passive pawl allows the plunger to move through the fourth opening because the passive pawl pivots and is spring loaded via the second spring.

Once the bone material dispensing device is finished dispensing bone material, and the plunger is fully retracted into the housing, the tubular member is also movable in a second position, as shown by arrow FF in FIG. 3 to misalign the proximal opening of the tubular member with the second opening of the housing to prevent the tubular member from receiving at least the portion of the plunger.

In some embodiments, the funnel is configured to be unlocked/released from the bone material dispensing device by the user in vivo. The unlocking/release of the funnel in vivo allows the user to remove the folding cannula while using the tray to load a new folding cannula into the tubular member. The funnel can then be locked/reattached to the bone material dispensing device without having to remove the funnel from the patient. This reduction in potential trauma or damage to soft tissues, particularly nerves, during funnel placement is beneficial. Unlocking/release of the funnel in vivo also reduces the amount of steps required in a surgical procedure.

In some embodiments, the bone material dispensing device can be used in conjunction with the products found and fully described in U.S. application Ser. Nos. 15/340,770, and 15/818,395; and U.S. Publication Nos. 2017/0216051, 2018/0078385, 2017/0216045, 2018/0071113, and 2016/0100955, of which are all owned by Applicant and incorporated fully herein by reference. In some embodiments, various orthopedic implants can be used in conjunction with the bone material dispensing device.

In some embodiments, the folding cannula can be made of a memory shape polymer and/or alloy to allow the folding cannula to move from an unfolded configuration to a folded configuration without the need for a locking mechanism. Memory shape polymers include, but are not limited to polyethers, polyacrylates, polyamides, polysiloxanes, polyurethanes, polyethers amides, polyurethane/ureas, polyether esters, polynorborene, cross-linked polymers such as cross-linked polyethylene and cross-linked poly(cyclooctene), inorganic-organic hybrid polymers, and copolymers such as urethane/butadiene copolymers, styrene-butadiene copolymers. Memory shape alloys include, but are not limited to TiNi, CuZnAl, and FeNiAl alloys. In some embodiments, the folding cannula can be fabricated by, but not be limited to, injection molding of plastic materials comprising rigid, surgical grade plastic and/or metal materials.

In some embodiments, components of the bone material dispensing system may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The folding cannula, funnel portion, plunger or tubular member may optionally include one or more tapered regions. In various embodiments, these components may be blunt, beveled, diamond point, ball tip, trocar tip, etc. These components may also have a tip style vital for accurate treatment of the patient depending on the surgical site. Examples of tip styles include, for example, Trephine, Cournand, Veress, Huber, Seldinger, Chiba, Francine, Bias, Crawford, deflected tips, Hustead, Lancet, or Tuohey. In some embodiments, the bone material dispensing device and tray can be made from materials that allow the bone material dispensing device to be reusable, or alternatively made from materials that allow for a single, disposable use.

In some embodiments, the shape of the folding cannula may be selected for particular applications. Such shape and configuration may include, for example, the basic shape of a folding cannula (e.g., a tubular shaped cannula).

Methods

A method of implanting a bone material is provided. The method comprising loading a bone material dispensing gun with the bone material from a tray, the bone material dispensing gun comprising a housing having a proximal end, a distal end, and a longitudinal axis, the proximal end having a first opening and the distal end having a second opening, the first opening and the second opening configured to slidably receive at least a portion of a plunger, and a locking member pivotably connected to an upper surface of the housing and extending adjacent to the upper surface from the housing, the locking member comprising a locking surface extending adjacent to the distal end of the housing configured to engage a portion of a tubular member, a funnel, or a combination thereof, the locking member being movable in a locking position, such as a downward position to lock the portion of the tubular member, the funnel, or the combination thereof to the housing, the tubular member being movable in a first position to align the proximal opening of the tubular member or the proximal opening of the tubular member and the funnel with the second opening of the housing to allow the tubular member or the tubular member and the funnel to receive at least the portion of the plunger to dispense the bone material.

In some embodiments, loading of the bone material dispensing gun with the bone material via the tray comprises engaging the tubular member with a slot of the tray, engaging a portion of the plunger with a ledge defined by a lower surface of the tray, and adding the bone material to an upper surface of the tray such that the bone material can be loaded into the tubular member and/or a cannula.

When the driving handle is pivoted, the driving pawl moves a defined amount. If a translation distance X is multiplied by a diameter of the funnel portion or the cannula, a cylinder of volume can be calculated. The bone material dispensing device can be adjusted to dispense a predefined amount of bone material per pivot of the driving handle. In some embodiments, the predefined amount of bone material dispensed from the bone material dispensing device can be of from about 0.25 cc to about 1 cc or from about 0.25 ounces (oz) to about 1 oz.

In some embodiments, the bone material can be dispensed in a quantifiable, controlled and predefined amount of from about 0.25 cc to about 1 cc. The bone material may be dispensed in a quantifiable, controlled and predefined amount of from about 0.25, 0.30, 0.35, 0.40, 0.45, 0.50, 0.55, 0.60, 0.65, 0.70, 0.75, 0.80, 0.85, 0.90, 0.95 to about 1 cc. In some embodiments, the bone material can be dispensed in a quantifiable, controlled and predefined amount of from about 0.25 oz to about 1 oz. The bone material may be dispensed in a quantifiable, controlled and predefined amount of from about 0.25, 0.30, 0.35, 0.40, 0.45, 0.50, 0.55, 0.60, 0.65, 0.70, 0.75, 0.80, 0.85, 0.90, 0.95 to about 1 oz.

The bone material can be mixed with liquid material and optionally a therapeutic agent until a desired consistency of the bone material is achieved (e.g., putty, paste, etc.). The bone material can be mixed with a suitable diluent and then loaded. The folding cannula may have enough space to allow for the bone material and a volume of diluent to be mixed. In some embodiments, the diluent includes dextrose, other sugars including but not limited to sucrose, fructose, glucose, lactated ringer's, polyols including, but not limited to, mannitol, xylitol, sorbitol, maltitol, lactitol, polysaccharides including but not limited to native or pre-gelatinized starch, maltodextrins, cyclodextrins, mineral compounds including, but not limited to, dicalcium or tricalcium phosphate, either dihydrate or anhydrous, cellulose derivatives including but not limited to microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline or 0.45% saline. In some embodiments, other delivery vehicles can be used for example, D5W (dextrose in 5% water), D5NS (dextrose in 5% water and normal saline) and D5W/½NS (D5W and ½ normal saline), blood, mesenchymal stem cells, or the like.

In various embodiments, a kit is provided comprising the bone material dispensing system. The kit may include additional parts along with the bone material dispensing device including the bone material, the tray and other components to be used to administer the bone material (e.g., wipes, needles, syringes, other mixing devices, etc.). The kit may include the bone material dispensing device in a first compartment. The second compartment may include the bone material. The third compartment may include the tray used for loading the bone material dispensing device with the bone material. In some embodiments, the shape of the tray may be selected for particular applications. Such shape and configuration may include, for example, the basic shape of a tray (e.g., a square shaped box, etc.). The tray can include additional features such as the tray and features found and fully described in U.S. application Ser. No. 15/581,817, which is owned by Applicant and incorporated fully herein by reference.

The fourth compartment may include a container for holding the bone material and/or a vial for holding any other instruments needed for the delivery. A fifth compartment may include gloves, drapes, wound dressings and other procedural supplies for maintaining sterility of the implanting process, as well as an instruction booklet, which may include a chart that shows how to administer the bone material after mixing it. A sixth compartment may include the spatula, needles, additional devices and/or sutures. Each tool may be separately packaged in a plastic pouch that is sterilized. A seventh compartment may include an agent for radiographic imaging. A cover of the kit may include illustrations of the dispensing/administering procedure and a clear plastic cover may be placed over the compartments to maintain sterility.

In various embodiments, one or more components of the bone material dispensing system is sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrate deeply into the bone material dispensing device. Gamma rays are highly effective in killing microorganisms, they leave no residues, nor do they have sufficient energy to impart radioactivity to the apparatus. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the bone material dispensing device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the bone material dispensing system including, but not limited to, gas sterilization such as, for example, with ethylene oxide or steam sterilization.

The bone material dispensing system can be used to treat a variety of conditions including osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders where native bone growth is inadequate, which will be evident to those of ordinary skill in the art. The bone material can be administered to treat open fractures and fractures at high risk of non-union, and in subjects with spinal disorders, including subjects in need of spine fusion (e.g., anterior lumbar interbody fusion, posterior lumbar spinal fusion, and cervical spine fusion) or subjects having degenerative disc disease or arthritis affecting the lumbar and cervical spine.

Bone Material

In some embodiments, the bone material can be demineralized bone material. The demineralized bone material can comprise demineralized bone, powder, chips, granules, shards, fibers or other shapes having irregular or random geometries. These can include, for example, substantially demineralized, partially demineralized, or fully demineralized cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in, for example, U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance the elongated demineralized bone fibers can be round, spherical, granular, elongated, powders, chips, fibers, cylinders, threads, narrow strips, thin sheets, or a combination thereof. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material comprises demineralized bone matrix fibers and demineralized bone matrix chips in a 30:60 ratio. In some embodiments, the bone material comprises demineralized bone matrix fibers and demineralized bone matrix chips in a ratio of 25:75 to about 75:25 fibers to chips.

In some embodiments, the bone material can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone material can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

In some embodiments, the bone material may be seeded with harvested bone cells and/or bone tissue, such as for example, cortical bone, autogenous bone, allogenic bones and/or xenogeneic bone while it is mixed.

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof. Recombinant BMP-2 can be used at a concentration of about 0.4 mg/mL to about 10.0 mg/mL, preferably about 1.5 mg/mL.

The bone material may include or be mixed with one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Application Publication No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride;

erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Although the invention has been described with reference to embodiments, persons skilled in the art will recognize that changes may be made in form and detail without departing from the spirit and scope of the disclosure.

What is claimed is:

1. A method of implanting a bone material, the method comprising: loading a bone material dispensing gun with the bone material from a tray, the bone material dispensing gun comprising a housing having a proximal end, a distal end, and a longitudinal axis, the proximal end having a first opening and the distal end having a second opening, the first opening and the second opening configured to slidably receive at least a portion of a plunger, and a locking member pivotably connected to an upper surface of the housing and extending adjacent to the upper surface from the housing, the locking member comprising a locking surface extending adjacent to the distal end of the housing configured to engage a portion of a tubular member, a funnel, or a combination thereof, the locking member being movable in a locking position, such as a downward position to lock the portion of the tubular member, the funnel, or the combination thereof to the housing, the tubular member being movable in a first position to align the proximal opening of the tubular member or the proximal opening of the tubular member and the funnel with the second opening of the housing to allow the tubular member or the tubular member and the funnel to receive at least the portion of the plunger to dispense the bone material.

2. The method of implanting bone material of claim 1, wherein (i) the loading of the bone material dispensing gun with the bone material via the tray comprises engaging the tubular member with a slot of the tray, engaging a portion of the plunger with a ledge defined by a lower surface of the tray, and adding the bone material to an upper surface of the tray such that the bone material can be loaded into the tubular member and/or a cannula; or (ii) the funnel is configured to be unlocked from the bone material dispensing device by the user in vivo.

3. The method of implanting bone material of claim 1, wherein the method further comprises moving the locking member in a downward position, which is the locking position and moving the locking member in an upward position, which is an unlocking position to unlock the portion of the tubular member, the funnel, or the combination thereof from the housing.

4. The method of implanting bone material of claim 1, wherein the locking member includes an interior surface comprising a stanchion at a proximal end, and a portion of the upper surface of the proximal end of the housing includes a recess, the stanchion and the recess configured for engagement with a first resilient member.

5. The method of implanting bone material of claim 1, wherein the locking member includes an intermediate portion, the intermediate portion comprising a pivot point engaged with the upper surface of the housing.

6. The method of implanting bone material of claim 1, wherein a distal end of the locking member includes the locking surface, the locking surface comprising a flange.

7. The method of implanting bone material of claim 1, wherein the tubular member comprises a proximal opening, a distal opening and a channel disposed therebetween, the proximal opening, the distal opening and the channel of the tubular member configured to receive at least the portion of the plunger.

8. The method of implanting bone material of claim 7, wherein the tubular member is movable in a first position to align the proximal opening of the tubular member with the second opening of the housing to allow the tubular member to receive at least the portion of the plunger to dispense the bone material, and the tubular member is movable in a second position to misalign the proximal opening of the tubular member with the second opening of the housing to prevent the tubular member from receiving at least the portion of the plunger.

9. The method of implanting bone material of claim 8, wherein the funnel is configured to partially enclose the tubular member.

10. The method of implanting bone material of claim 8, wherein the funnel comprises a distal end having a tip geometry, the distal end tip geometry of the funnel being indented.

11. The method of implanting bone material of claim 1, wherein the tubular member and/or the funnel is configured to engage a cannula.

12. The method of implanting bone material of claim 11, wherein the cannula comprises a folding cannula.

13. The method of implanting bone material of claim 12, wherein the folding cannula has a diameter larger than a diameter of the distal opening of the tubular member so as to allow at least a portion of the folding cannula to be held within the tubular member.

14. The method of implanting bone material of claim 1, wherein the housing comprises a trigger assembly configured to allow incremental slidable movement of the plunger to dispense the bone material.

15. The method of implanting bone material of claim 14, wherein the trigger assembly comprises a driving handle, a stationary handle, a driving pawl, a passive pawl, a second resilient member disposed between a first portion of the housing and the passive pawl, and a third resilient member concentric to the plunger and the second resilient member, and disposed between a second portion of the housing and the driving pawl, the driving handle configured to contact the driving pawl when the driving handle is moved toward the stationary handle, wherein movement of the driving handle toward the stationary handle causes the driving pawl to compress the third resilient member and allow incremental slidable movement of the plunger.

16. The method of implanting bone material of claim 15, wherein movement of the driving handle toward the stationary handle causes the second resilient member to be compressed against the first portion of the housing by the passive pawl.

17. The method of implanting bone material of claim 1, wherein the plunger comprises a proximal end and a distal end, the proximal end including a stopper.

18. A method of implanting a bone material, the method comprising loading a bone material to a bone material dispensing system comprising a bone material dispensing device comprising a housing having a proximal end, a distal end, and a longitudinal axis, the proximal end having a first opening and the distal end having a second opening, the first opening and the second opening configured to slidably receive at least a portion of a plunger, and a locking member pivotably connected to an upper surface of the housing and extending adjacent to the upper surface of the housing, the locking member comprising a locking surface extending adjacent to the distal end of the housing, the locking member being movable in a locking position to lock the portion of the tubular member, the funnel, or the combination thereof with the housing; and a tray engageable with the bone material dispensing device for loading the bone material dispensing device with bone material.

19. The method of implanting bone material of claim 18, wherein the tray is engageable with a distal end of the tubular member and the plunger.

20. The method of implanting bone material of claim 19, wherein the tray comprises a slot configured to receive the tubular member, a ledge on a lower surface of the tray configured to receive a portion of the plunger, an upper surface configured for dispensing the bone material, and a groove defined from the upper surface configured to receive a cannula.

* * * * *